(12) United States Patent
Reddy et al.

(10) Patent No.: US 6,706,927 B2
(45) Date of Patent: Mar. 16, 2004

(54) ALKYNE KETONES

(75) Inventors: M. V. Ramana Reddy, Upper Darby, PA (US); Stanley C. Bell, Narberth, PA (US)

(73) Assignee: Onconova Therapeutics, Inc., Lawrenceville, NJ (US)

( * ) Notice: Subject to any disclaimer, the term of this patent is extended or adjusted under 35 U.S.C. 154(b) by 0 days.

(21) Appl. No.: 10/423,790

(22) Filed: Apr. 25, 2003

(65) Prior Publication Data

US 2003/0199707 A1 Oct. 23, 2003

Related U.S. Application Data

(62) Division of application No. 10/245,949, filed on Sep. 18, 2002, now Pat. No. 6,579,988.
(60) Provisional application No. 60/323,006, filed on Sep. 18, 2001.

(51) Int. Cl.[7] ............................................. C07C 49/235
(52) U.S. Cl. ..................... 568/308; 548/377.1
(58) Field of Search ......................................... 568/308

(56) References Cited

U.S. PATENT DOCUMENTS

| 2,974,141 | A | 3/1961 | Pine | |
|---|---|---|---|---|
| 5,563,165 | A | 10/1996 | Talley et al. | 514/406 |
| 5,932,598 | A | 8/1999 | Talley et al. | 514/341 |
| 6,060,605 | A | 5/2000 | Lantzch | |
| 6,376,519 | B1 | 4/2002 | Reddy et al. | 514/341 |
| 6,391,906 | B2 | 5/2002 | Gunduz et al. | |

FOREIGN PATENT DOCUMENTS

WO WO 9746534 12/1997

OTHER PUBLICATIONS

Linderman et al, *Chemical Abstracts*, vol 112, No. 72250, 1990.*
Penning, et al. 1997. J. Med. Chem. 40:1347–1365 "Synthesis and Biological Evaluation of the 1,5–Diarylpyrazole Class of Cyclooxygenase–2 Inhibitors: Identification of 4–[5–(4–Methylphenyl–3–(trifluoromethyl)–1H–pyrazol–1–yl]benzenesulfonamide (SC–58635, Celecoxib)".
Talley, et al. 2000. J. Med. Chem. 43:1661–1663 "N–[[(5–Methyl–3–phenylisoxazol–4–yl)–phenyl]sulfonyl]propanamide, sodium salt, parecoxib sodium: A potent and selective inhibitor of COX–2 for parenteral administration".
SciFinder Search (Jul. 22, 2003).
Li, Qing X. et al, Structure Activity Studies . . . , Bioorganic & Medicinal Chemistry, 1994, 2(12), pp 1423–1424.—Abstract Only.
Shen, Yanchang et al, Studies of the Application . . . , Synthesis, 1984, 1, pp 35–37—Abstract Only.
Kitazume Tomoya et al., A Convenient Synthesis . . . , Chemistry Letters, 1980, 10, 1327–1328.

* cited by examiner

*Primary Examiner*—Robert W. Ramsuer
(74) *Attorney, Agent, or Firm*—Dechert LLP; Eric A. Meade

(57) ABSTRACT

Provided are processes for the preparation of the compound of the formula

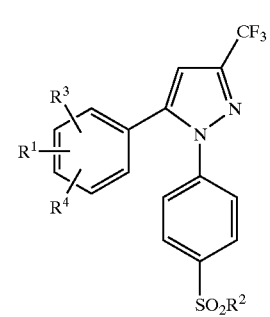

1 wherein $R^1$, $R^3$ and $R^4$ are independently selected from the group consisting of hydrogen, halogen, hydroxyl, nitro, lower alkyl, lower alkoxy, carboxy, $C_1$–$C_6$ trihaloalkyl, and cyano; and $R^2$ is amino or lower alkyl.

Also provided are synthetic intermediates that are useful as intermediates in the preparation of the compound of the formula 1.

2 Claims, No Drawings

ALKYNE KETONES

This application is a divisional of U.S. patent application Ser. No. 10/245,949, filed Sep. 18, 2002, now U.S. Pat. No. 6,579,988, which claims the benefit of U.S. patent application Ser. No. 60/323,006, filed Sep. 18, 2001. The disclosure of both of these applications are hereby incorporated by reference as if fully set forth herein.

The present invention relates to processes for the preparation of 1,5-diarylpyrazoles, and chemical intermediates that serve as useful intermediates in the preparation of 1,5-diarylpyrazoles. 1,5-Diarylpyrazoles are particularly useful in the treatment of inflammation and inflammation-related disorders, including arthritis.

Selective inhibitors of cyclooxygenase-2 (COX-2) have demonstrated effective anti-inflammatory activity with reduced gastrointestinal side effects, as compared to other antiinflammatory agents, e.g., NSAIDs, that inhibit both the constitutive form of cyclooxygenase (COX-1), and the inducible form of the enzyme, COX-2. A particularly effective structural class of selective COX-2 inhibitors are the 1,5-diarylpyrazoles. For example, the compound, 4-[5-(4-methylphenyl)-3-(trifluoromethyl)-1H-pyrazol-1-yl]benzenesulfonamide (celecoxib®) has been approved by the Food and Drug Administration for the treatment of rheumatoid arthritis and osteoarthritis.

Penning et al. (*J. Med. Chem.* 1997, 40, 1347–1365) discloses that 1,5-diarylpyrazoles can be prepared by condensation of 1,3-dicarbonyl adducts with aryl hydrazines. The 1,3-dicarbonyl adducts can be prepared by Claisen condensations of aryl methyl ketones with carboxylic acid esters. In an alternate preparation, the 1,5-diarylpyrazoles can be synthesized by epoxidation of β-aryl-α,β-unsaturated ketones, followed by condensation of the resulting epoxides with arylhydrazines.

SUMMARY OF THE INVENTION

In one embodiment, the invention relates to a process for preparing a compound of the formula

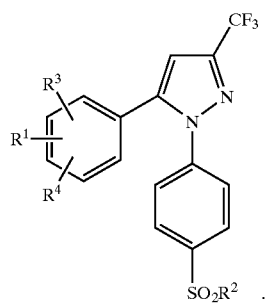

1

$R^1$, $R^3$ and $R^4$ are independently selected from the group consisting of hydrogen; halogen; preferably fluoro, chloro, bromo or iodo; hydroxyl; nitro; $C_1$ to $C_6$ alkyl, preferably $C_1$ to $C_3$ alkyl; $C_1$ to $C_6$ alkoxy, preferably $C_1$ to $C_3$ alkoxy, more preferably methoxy; carboxy; $C_1$–$C_6$ trihaloalkyl, preferably trihalomethyl, more preferably trifluoromethyl; and cyano.

$R^2$ is amino; or lower alkyl, preferably $C_1$ to $C_3$ alkyl.

In preferred aspects, the invention relates to the process for preparing a compound having the formula

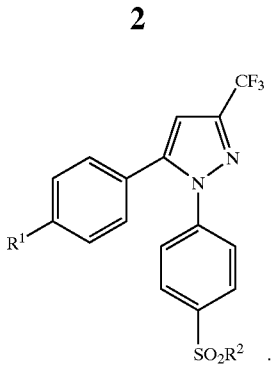

Preferably $R^1$ is methyl, particularly where $R^2$ is amino.

The process includes the step of condensing an alkyne of formula

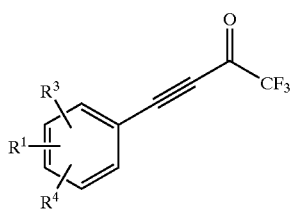

3 with a phenyl hydrazine of the formula

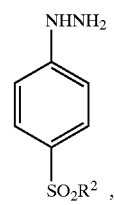

4 or a salt thereof.

In some embodiments, the alkyne of the formula 3 is prepared by:
(i) adding bromine to a compound of formula

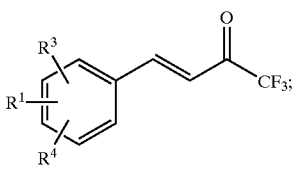

2 and
(ii) contacting the product of step (i) with a base.

In one embodiment, the compound of the formula 2 can be prepared by treating a compound of the formula

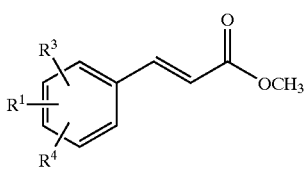

5 with trimethyl(trifluoromethyl)silane in the presence of cesium fluoride.

In an alternative embodiment, the compound of formula 3 can be prepared by a process that includes:
(i) contacting a phenylacetylene of the formula

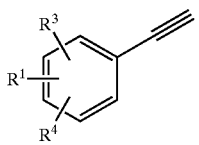
10 with carbon monoxide, oxygen, and methanol, in the presence of a palladium (II) catalyst to provide a propargylic ester of the formula

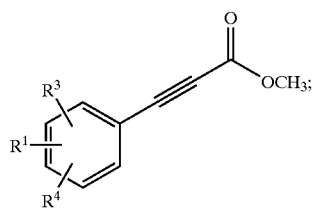
9 and
(ii) treating the propargylic ester of the formula 9 with trimethyl(trifluoromethyl)silane in the presence of cesium fluoride to give the compound of formula 3.

In another aspect, the invention relates to a compound of the formula

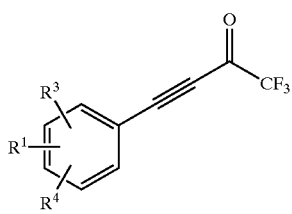
3

$R^1$, $R^3$ and $R^4$ are independently selected from the group consisting of hydrogen; halogen; preferably fluoro, chloro, bromo or iodo; hydroxyl; nitro; $C_1$ to $C_6$ alkyl, preferably $C_1$ to $C_3$ alkyl; $C_1$ to $C_6$ alkoxy, preferably $C_1$ to $C_3$ alkoxy, more preferably methoxy; carboxy; $C_1$–$C_6$ trihaloalkyl, preferably trihalomethyl, more preferably trifluoromethyl; and cyano.

In a preferred embodiment, the compound has the formula

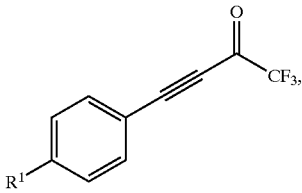

wherein $R^1$ is lower alkyl, preferably methyl.

DETAILED DESCRIPTION OF THE INVENTION

The following terms shall have, for the purposes of this application, the respective meanings set forth below.

"lower alkoxy" shall include linear or branched $C_1$ to $C_6$ alkoxy groups, unless otherwise specified.

"lower alkyl" shall include linear or branched $C_1$ to $C_6$ alkyl groups, unless otherwise specified.

In accordance with the present invention, novel processes and synthetic intermediates for the preparation of 1,5-diarylpyrazoles are provided. The processes of the invention have been developed from readily available and inexpensive starting materials. Furthermore, the processes provide high yields of 1,5-diarylpyrazoles, and simplify isolation and purification steps.

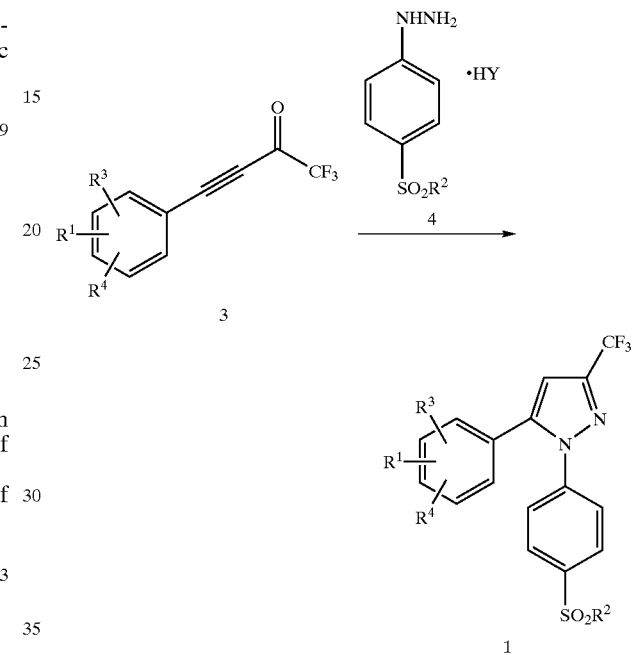

Scheme 1

One embodiment of the invention is depicted in Scheme 1, wherein $R^1$–$R^4$ are as described above for the compound of formula 1, and Y is a halide, preferably chloride. An alkyne of the formula 3, is condensed with a phenyl hydrazine compound of the formula 4 to provide a 1,5-diaryl-3-trifluoromethylpyrazole of the formula 1. Preferably, the phenyl hydrazine compound of the formula 4 is provided as a salt, e.g., a hydrochloride salt. The reaction can be completed in a protic solvent such as ethanol, n-propanol, isopropanol, butanol or acetic acid at an elevated temperature, e.g. ethanol at reflux. Typically a slight excess of phenyl hydrazine is used, from about 1.05 to about 1.3 molar equivalents. The reaction provides high regioselectivity with respect to the ratio of products obtained of the 1,5-diaryl type (i.e. compound of the formula 1) to the 1,3-diaryl type (not shown). Typically, the ratio of the desired 1,5-diaryl pyrazole to the undesired 1,3-isomer is greater than 9 to 1. Purification of the compound of formula 1 can be conveniently carried out by recrystallization from alcohol solvents, e.g., ethanol.

Various acid addition salts of the compound of the formula 1 can be prepared by treatment with an organic or inorganic acid. Preferably, the acid addition salts formed are pharmaceutically acceptable salts, such as those described in U.S. Pat. No. 5,563,165, the disclosure of which is herein incorporated by reference. Suitable base addition salts of the compound of formula 1, wherein the phenyl group at the 5-position of the pyrazole ring incorporates a carboxy or hydroxyl substituent. Base addition salts include metallic addition salts, e.g, sodium, potassium, and organic base addition salts, e.g, organic amines. Other pharmaceutically acceptable acid addition salts are detailed in U.S. Pat. No. 5,563,165.

The phenyl hydrazine compound of the formula 4 can be prepared from substituted anilines of the formula 11, wherein $R^2$ is amino or lower alkyl as shown in Scheme 2. Preferably, the aniline contains the amidosulfonyl or alkylsulfonyl group in the para position as shown in the structural formula for 11. A diazonium salt is formed from the substituted aniline by treatment with nitrous acid (e.g., formed from hydrochloric acid and sodium nitrite). For example, an aqueous mixture of sulfanilamide and hydrochloric acid is treated with a solution of sodium nitrite at temperatures below about 5° C. to form the corresponding diazonium salt. The cold diazonium salt is then treated with a reducing agent, e.g., stannous chloride, to provide the substituted phenyl hydrazine compound. It will be appreciated that alternative well-known preparations of phenyl hydrazine compounds can also be used, for example, preparation from phenyl halides by nucleophilic displacement by hydrazine.

Scheme 2

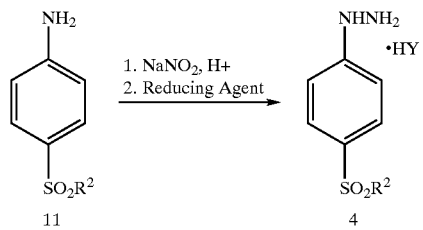

The alkyne of the formula 3 can be prepared by synthetic methods that are depicted in Schemes 3 and 4. In one embodiment, the alkyne of the formula 3 is obtained from an α,β-unsaturated ketone precursor, the compound of formula 2 (Scheme 3). The compound of formula 2, for example, is first treated with bromine in a suitable inert organic solvent, e.g. chloroform, at room temperature for a sufficient amount of time to form an α,β-dibromo intermediate. The crude product obtained from the bromination reaction is subsequently treated with a base such an alkali metal hydroxide, e.g., potassium, sodium, or lithium hydroxide, to effect elimination of HBr and provide the alkyne of formula 3. The alkyne of the formula 3 can be further purified by, for example, recrystallization from suitable solvents, e.g., alcohols, when the compound is a solid. Alternatively, the compound of the formula 3 can be purified by, for example, chromatography.

Scheme 3

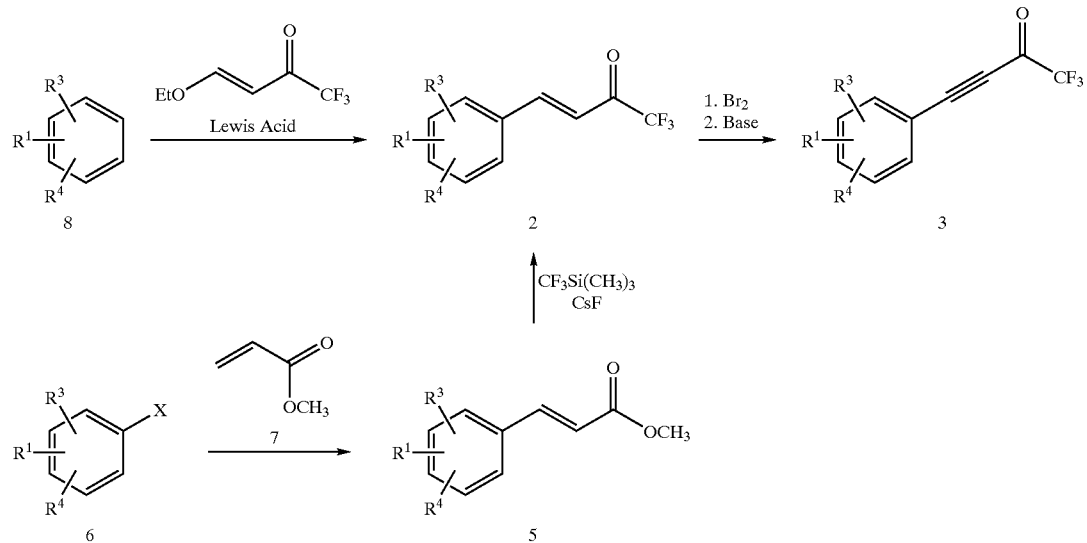

In one embodiment, the compound of formula 2 can be obtained by electrophilic addition of a vinylogous ester, 4-ethoxy-1,1,1-trifluoro-3-buten-2-one, to the substituted phenyl compound of the formula 8. For example, toluene ($R^1$=methyl) can be treated with an equimolar amount of 4-ethoxy-1,1,1-trifluoro-3-buten-2-one in a suitable inert solvent, e.g., dichloromethane, to provide 1,1,1-trifluoro-4-(4-methylphenyl)-3-buten-2-one. Typically, a catalytic amount, e.g. <10 mole %, of a Lewis acid, e.g., zinc chloride, is added to the reaction mixture to catalyze the addition.

In this embodiment and an all other embodiments suitable protecting groups, well known in the art, can be used, where necessary, to protect various phenyl substituents (i.e., $R^1$, $R^3$ and $R^4$), which are then removed later in the synthesis by known methods. Thus, for example, a hydroxyl moiety can be protected as a methyl or silyl ether. Similarly, a carboxy moiety can be protected as an ester if necessary, which can be hydrolyzed in a later in a later synthetic step.

In another embodiment, the compound of formula 2 is obtained from a cinnamic acid ester of the formula 5, by treatment with trimethyl(1,1,1-trifluoromethyl)silane and cesium fluoride (Scheme 3). The reaction is carried out neat, or in an inert organic solvent, e.g, dichloromethane, tetrahydrofuran, at a temperature of about 15 to about 30° C. The cinnamic acid ester can be obtained from a Heck coupling of a halophenyl compound of the formula 6 (wherein X is Cl, Br, or I, preferably Br or I) with an alkyl acrylate of the formula 7. The reaction mixture includes a base, e.g., potassium carbonate, and a palladium catalyst. Palladium catalysts for the Heck reaction are well-known and include palladium(II) acetate. A stabilizing ligand for the palladium such as triphenylphosphine can be included in the reaction mixture, include A preferred catalyst is Pd—Cu-Mont. K-10 (clay). The reaction is typically carried out in a dipolar aprotic solvent e.g., dimethylfornamide, at temperatures of about 100 to about 160° C. The Heck procedure permits regioselective coupling of the alkyl acrylate group on to the phenyl ring. This procedure is particularly advantageous for compounds wherein the electrophilic addition of the vinylogous ester to the phenyl precursors 8 described above leads to unfavorable mixtures of regioisomers in the product.

In another embodiment of the invention, the alkyne of the formula 3 is obtained by treatment of a propargylic ester of the formula 9, with trimethyl(1,1,1-trifluoromethyl)silane and cesium fluoride (Scheme 4). Here again, the reaction is carried out neat, or in an inert organic solvent, e.g., dichloromethane, tetrahydrofuran, at a temperature of about 15 to about 30° C.

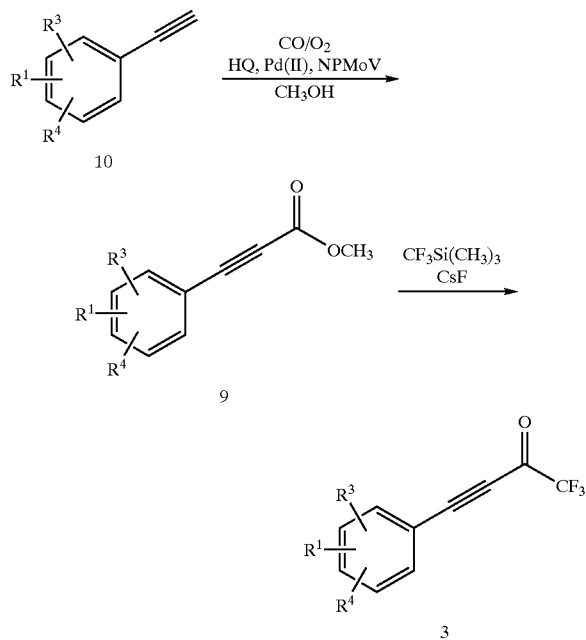

Scheme 4

The propargylic ester of the formula 9 can be obtained from a phenylacetylene having the formula 10, wherein $R^1$ is as described above. The reaction is catalyzed by a palladium (II) catalyst, e.g., palladium (II) acetate, in a methanol at a temperature of about 15° C. to about 40° C. Preferably, the reaction catalyzed by a palladium (II) catalyst (e.g., palladium (II) acetate), molybdovanadophosphate (NPMoV), and chlorohydroquinone (HQ-Cl).

In another embodiment, the propargylic ester of the formula 9, may be obtained by formation of the corresponding anion of the alkyne having the formula 10, with a strong base, e.g., n-butyllithium, lithium diisopropylamide, lithium hexamethyl-disilazide, and addition of the anion to an activated derivative of trifluoracetic acid, e.g, trifluoroacetyl chloride, trifluoroacetic anhydride.

The following examples further illustrate the present invention, but of course, should not be construed as in any way limiting its scope.

EXAMPLE 1

Synthesis of 4-[5-(4-methylphenyl)-3-(trifluoromethyl)-1H-pyrazol-1-yl] benzenesulfonamide ($R^1$=p-$CH_3$ and $R^2$=$NH_2$, $R^3$=$R^4$=H)

Preparation of 1,1,1-Trifluoro-4-(4-methylphenyl)-3-buten-2-one (2, $R^1$=p-$CH_3$, $R^3$=$R^4$=H)

To a solution of toluene (8, $R^1$=p-$CH_3$, $R^3$=$R^4$=H, 10 mmol) and 4-ethoxy-1,1,1-trifluoro-3-buten-2-one (10 mmol) in dichloromethane (10 mL) is added zinc chloride (0.015 g, 1.5 mol %). The reaction mixture is stirred for 3 h at 22° C. The resulting precipitate is filtered, washed with dichloromethane (2×15 mL) and dried.

Preparation of 1,1,1-Trifluoro-4-(4-methylphenyl)-3-butyn-2-one (3, $R^1$=p-$CH_3$, $R^3$=$R^4$=H)

To a stirred solution of 1,1,1-trifluoro-4-(4-methylphenyl)-3-buten-2-one (2, 10 mmol) in chloroform (100 mL), a solution of bromine(10 mmol) in chloroform (50 mL) is added dropwise at room temperature. The solution is stirred for an additional 30 min to complete of the reaction. The solvent is then removed under vacuum to obtain the dibromo compound.

The dibromo compound is added in portions to a solution of ethanolic (200 mL) potassium hydroxide (10 mmol) over a period of 30 min. After the addition is complete, the reaction mixture is refluxed for 3 h, cooled and poured onto ice cold water. The precipitated 1,1,1-trifluoro-4-(methylphenyl)-3-butyn-2-one is separated by filtration and recrystallized.

Preparation of 4-Sulfamylphenyl hydrazine Hydrochloride (4, $R^2$=$NH_2$)

(A procedure is described in *J. Med Chem*. 1979, 22, 321–325.) A cold stirred mixture of sulfanilamide (11, 34.2 g, 0.2 mol), hydrochloric acid (100 mL) and crushed ice (200 g) is diazotized by dropwise addition of sodium nitrite (14 g, 0.2 mol) in water (25 mL) over 30 min. The cold diazonium salt thus formed is rapidly added to a well-cooled solution of stannous chloride (100 g) in hydrochloric acid (150 mL) with vigorous stirring, and the resulting mixture is left in the refrigerator overnight. The precipitated 4-sulfamylphenyl hydrazine hydrochloride is collected at pump and dried.

Preparation of 4-[5-(4-methylphenyl)-3-(trifluoromethyl)-1H-pyrazol-1-yl] benzenesulfonamide (1, $R^1$=$CH_3$, $R^3$=$R^4$=H and $R^2$=$NH_2$)

A solution of 1,1,1-trifluoro-4-(methylphenyl)-3-butyn-2-one (3, 10 mmol) in ethanol (100 mL) is refluxed with 4-sulfamylphenyl hydrazine hydrochloride (4, 12 mmol) for 4 h. The reaction mixture is cooled and diluted with water. The precipitated crude 4-[5-(4-methylphenyl)-3-(trifluoromethyl)-1H-pyrazol-1-yl]benzenesulfonamide is filtered and recrystallized.

EXAMPLE 2

Preparation of 1,1,1-Trifluoro-4-Phenyl-3-Butyn-2-one (3, $R^1$=H)

Preparation of Methyl phenylpropiolate (9, $R^1$=H, $R^3$=$R^4$=H)

A solution of phenylacetylene (10, 2 mmol), chlorohydroquinone(HQ-Cl) (0.4 mmol), molybdovanadophosphate (NPMoV) (35 mg) and palladium (II) acetate (50 mg) in methanol (10 mL) is stirred under $CO/O_2$ (10 atm/0.5 atm) at 25° C. for 15 h. The reaction is then quenched with wet ether and the product is extracted with n-hexane. After removal of the solvent under reduced pressure, the product is isolated by column chromatography over silica gel (hexane:ethyl acetate 5:1) to give pure methyl phenylpropiolate.

Conversion of Methyl Phenylpropiolate (9) to 1,1,1-Trifluoro-4-phenyl-3-butyn-2-one (3)

At room temperature, CsF (0.15 g, 1 mmol) is added to a mixture of methyl phenylpropiolate (9, 1.62 g, 10 mmol) and TMS-$CF_3$ (1.46 g, 10.25 mmol) (Lancaster). After completion of the reaction (3 h), hydrolysis is carried out over 3 h by using 4 N HCl (4 mL). The resulting product is extracted with ether (30 mL). After removing the ether, the trifluoromethylated ketone is obtained.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A compound of the formula

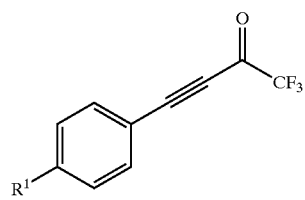

wherein $R^1$ is lower alkyl.

2. The compound of claim 1, wherein $R^1$ is methyl.

* * * * *